(12) United States Patent
Patterson

(10) Patent No.: US 6,329,167 B1
(45) Date of Patent: Dec. 11, 2001

(54) METHOD OF TESTING ADEQUACY OF CELLS IN A SPECIMEN

(76) Inventor: Bruce K. Patterson, 211 W. St. Paul, Apt 3, Chicago, IL (US) 60614

( * ) Notice: Subject to any disclaimer, the term of this patent is extended or adjusted under 35 U.S.C. 154(b) by 0 days.

(21) Appl. No.: 09/730,223

(22) Filed: Dec. 5, 2000

(51) Int. Cl.⁷ .............................. C12Q 1/04; C12Q 1/02; C12Q 1/00
(52) U.S. Cl. .................................... 435/34; 435/29; 435/4
(58) Field of Search ............................... 435/29, 4, 40.5, 435/6, 7.1, 14, 34

(56) References Cited

FOREIGN PATENT DOCUMENTS

363058258A * 3/1988 (JP) .............................. G01N/33/483

OTHER PUBLICATIONS

Barrett et al. Acta. Cytol. (1978) 22 (1) 7–14.*

* cited by examiner

Primary Examiner—Jon P. Weber
Assistant Examiner—Brett Ozga

(57) ABSTRACT

The present invention relates to an appartus and method for use in pre-screening or determining the adequacy of target cells in specimen prior to conducting further diagnostic testing or analysis of the specimen. More specifically, the present invention concerns a device and method which uses light scatter techniques to detect the presence of a target cell in a specimen.

17 Claims, 1 Drawing Sheet

METHOD OF TESTING ADEQUACY OF CELLS IN A SPECIMEN

BACKGROUND OF THE INVENTION

The present invention relates to an apparatus and method for use in pre-screening or determining the adequacy of target cells in a specimen prior to conducting further diagnostic testing or analysis of the specimen. More specifically, the present invention concerns a device and method which uses light scatter techniques to detect the presence of a target cell in a specimen.

SUMMARY OF THE INVENTION

Prior to conducting an analysis or testing of a cell specimen, it is important to insure that an adequate amount of target cells are present in the specimen. This is particularly true with respect to pap smear specimens.

It is estimated that about 180 million pap smears are performed in the United States annually with an estimated 33% of all specimens originally collected containing insufficient target cells—ectocervical or squamous cells. This results in an inability to properly analyze the specimen and in a tremendous loss in time and money. Typically, not only must a patient reschedule another office visit to provide a second specimen, a second charge is often incurred to obtain the second specimen with no guarantee that enough target cells were again obtained. Thus, there is a need to provide a method and apparatus which provides a quick and efficient system to pre-screen specimens to determine if adequate target cells are present.

The present invention solves this lack of pre-screening by providing a device and method which analyzes a specimen through the use of submitting the specimen to a light scatter analysis. Through this technique, a specimen may be analyzed for the presence of sufficient quantities of a target cell. In addition, the technique would also allow a specimen to be analyzed for the presence of target cells which may adversely affect the diagnostic procedure to be used.

DESCRIPTION OF THE DRAWINGS

These and other features, objects and advantages of the present invention will become apparent from the following description and drawings wherein like reference numerals represent like elements in several views, and in which.

DESCRIPTION OF THE PREFERRED EMBODIMENT

Figure 1:
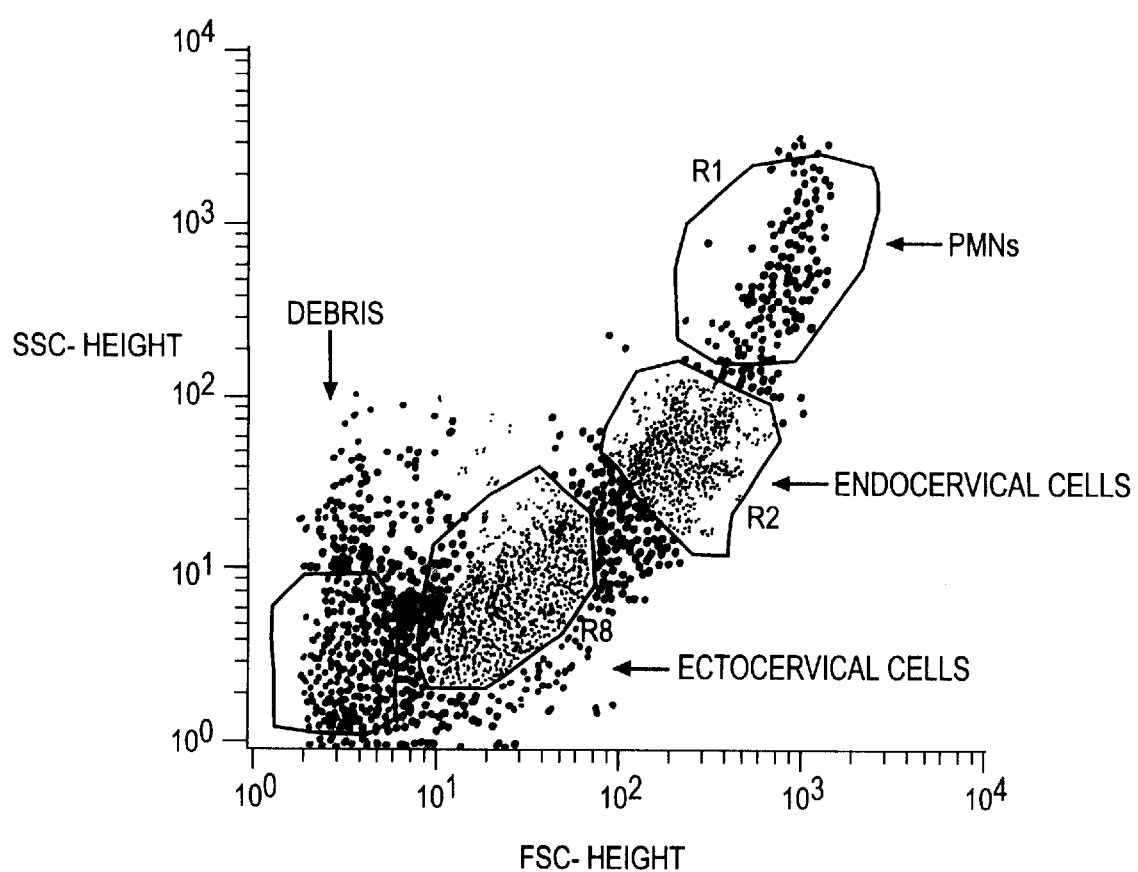
FIG. 1 shows a sample analysis using light scatter to locate a plurality of predetermined target cells.

Set forth below is a description of what are currently believed to be the preferred embodiments or best examples of the invention claimed. Future and present alternatives and modifications to the preferred embodiments are contemplated. Any alternates or modifications in which insubstantial changes in function, in purpose, in structure or in result are intended to be covered by the claims of this patent.

The present invention may be useful in pre-screening or determining the presence of target cells in sufficient quantities prior to subjecting the specimen to further testing. As explained above, screening specimens for adequate amounts of target cells or the presence of target cells which are adverse to a procedure, while a patient is still at a medical facility, will save both time and money.

To do this, the present invention uses a technique commonly referred to as light scatter. In this technique, a cell is subjected to light applied at a predetermined orientation. Because each cell has a specific morphology, when illuminated, the cell's morphology will cause light to be scattered in a predetermined pattern in both a forward and side direction. Thus, for each target cell of interest, a predetermined light scatter pattern can be established in a forward direction, side direction or both forward and side directions using flow cytometry and other similar techniques which are known to those of skill in the art.

Thus, in using the present invention, after a specimen is obtained, it can be quickly subjected to a light scatter technique to determine if adequate target cells are present for further testing purposes or if adverse target cells are present. As explained above, using this technique would increase the efficiency and cost-effectiveness of any testing procedure including, but not limited to, pap smear testing.

More specifically, to measure the adequacy of liquid based cervical cytology specimens such as in a pap smear specimen, 1 mL of the sample (usually 10 mL) routinely collected in industry standard preservatives (Cytyc, TriPath) may be pelleted by centrifugation at 500–1000×g and resuspended in 300 uL of phosphate buffer saline (PBS), pH 7.4. The sample is then run in a flow cytometer or the like for analysis of forward light scatter and side (90°) light scatter. Ectocervical (columnar) cells, endocervical (squamous) cells, neutrophils, and non-cellular material/debris are resolved into 4 cellular populations as shown in FIG. 1 using a log scale rather than a linear scale. The presence of both ectocervical and endocervical cells would indicate an adequate specimen. Conversely, the absence or the low amount of a predetermined light scatter pattern for a target cell would indicate that an inadequate specimen had been obtained and the collection procedure should be repeated. This process would take approximately 10 minutes.

While the preferred embodiments of the present invention have been illustrated and described, it will be understood by those of ordinary skill in the art that changes and other modifications can be made without departing from the invention in its broader aspects. Various features of the present invention are set forth in the following claims.

What is claimed is:

1. A method of pre-screening a specimen to determine an adequate number of squamous (ectocervical) cells, columnar (endocervical) cells, neutrophils, and noncellular material for subsequent liquid based cytology analysis comprising:

a. analyzing said liquid based cytology specimen using light scatter to quantify the number of different cells in said specimen; and b. determining if the quantity of squamous (ectocervical) cells versus columnar (endocervical) cells versus neutrophils versus noncellular material using the results of said light scatter is sufficient for liquid based cytology analysis.

2. The method of claim 1 wherein said light scatter characteristic is forward light scatter.

3. The method of claim 1 wherein said light scatter characteristic is side light scatter.

4. The method of claim 1 wherein said light scatter characteristic is both side and forward light scatter.

5. A method of pre-screening a specimen to determine an adequate number of at least one target cell for subsequent liquid based cytology analysis comprising:

analyzing said liquid based cytology specimen using light scatter to quantify the number of at least one target cell in said specimen; and determining if the quantity of at least one target cell in said specimen is sufficient for liquid based cytology analysis using the results of said light scatter.

6. The method of claim 5 wherein the target cell is an ectocervical cell.

7. The method of claim 5 wherein the target cell is an endocervical cell.

8. The method of claim 5 wherein the specimen is to be used in a cervical cancer screening test.

9. The method of claim 5 wherein said light scatter is forward light scatter.

10. The method of claim 5 wherein said light scatter is side light scatter.

11. The method of claim 5 wherein said light scatter is both side and forward light scatter.

12. A method of pre-screening a specimen to determine an adequate number of at least one target cell in a cervical cytology specimen for subsequent liquid based cytology analysis comprising:

analyzing said liquid based cervical cytology specimen using light scatter to quantify the number of at least one target cell in said specimen; and determining if the quantity of at least one target cell in said specimen is sufficient for liquid based cytology analysis using the results of said light scatter.

13. The method of claim 12 wherein the target cell is an ectocervical cell.

14. The method of claim 12 wherein the target cell is an endocervical cell.

15. The method of claim 12 wherein said light scatter is forward light scatter.

16. The method of claim 12 wherein said light scatter is side light scatter.

17. The method of claim 12 wherein said light scatter is both side and forward light scatter.

* * * * *